(12) United States Patent
Rajagopal et al.

(10) Patent No.: US 9,128,124 B2
(45) Date of Patent: Sep. 8, 2015

(54) WIRELESS VOLTAGE SENSING DEVICE

(71) Applicant: California Institute of Technology, Pasadena, CA (US)

(72) Inventors: Aditya Rajagopal, Irvine, CA (US); Chieh-Feng Chang, Pasadena, CA (US); Akram Sarwat Sadek, England (GB); Axel Scherer, Barnard, VT (US); Raymond Jimenez, Duarte, CA (US)

(73) Assignee: California Institute of Technology, Pasadena, CA (US)

( * ) Notice: Subject to any disclaimer, the term of this patent is extended or adjusted under 35 U.S.C. 154(b) by 94 days.

(21) Appl. No.: 13/764,612

(22) Filed: Feb. 11, 2013

(65) Prior Publication Data

US 2013/0207639 A1 Aug. 15, 2013

Related U.S. Application Data

(60) Provisional application No. 61/597,585, filed on Feb. 10, 2012.

(51) Int. Cl.
*G01R 19/20* (2006.01)
*G01R 19/00* (2006.01)
*A61B 5/04* (2006.01)
*A61B 5/00* (2006.01)

(52) U.S. Cl.
CPC .............. *G01R 19/00* (2013.01); *A61B 5/0031* (2013.01); *A61B 5/04001* (2013.01); *A61B 2560/0214* (2013.01); *A61B 2562/0209* (2013.01); *A61B 2562/0233* (2013.01); *A61B 2562/164* (2013.01); *A61B 2562/166* (2013.01); *A61B 2562/223* (2013.01)

(58) Field of Classification Search
CPC .............. A61B 5/0031; A61B 5/0017; A61B 2560/0219; A61B 5/0026; A61B 5/0408; A61B 8/4472; A61B 2562/00–2562/247; A61B 2560/00–2560/066; G01R 33/285; G01R 19/00–19/32
USPC ............... 324/72.5, 76.39, 97, 111, 444, 713, 324/522–530, 76.41–76.83
See application file for complete search history.

(56) References Cited

U.S. PATENT DOCUMENTS

| | | | |
|---|---|---|---|
| 6,575,965 B1* | 6/2003 | Fitch et al. ....................... | 606/15 |
| 7,212,851 B2* | 5/2007 | Donoghue et al. ............ | 600/544 |
| 2003/0100823 A1* | 5/2003 | Kipke et al. ................... | 600/378 |
| 2004/0006264 A1* | 1/2004 | Mojarradi et al. ............ | 600/378 |
| 2008/0154101 A1* | 6/2008 | Jain et al. ...................... | 600/309 |
| 2009/0021313 A1* | 1/2009 | Hung .............................. | 331/57 |
| 2009/0047023 A1* | 2/2009 | Pescod et al. ................. | 398/115 |
| 2010/0106041 A1* | 4/2010 | Ghovanloo et al. ........... | 600/544 |
| 2011/0255578 A1* | 10/2011 | Sorrells et al. ................ | 375/219 |

OTHER PUBLICATIONS

Henry, M. D., et al., "Alumina etch masks for fabrication of high-aspect-ratio silicon micropillars and nanopillars", Nanotechnology 20.25 (2009): 255305.
Walavalkar, S. S., et al., "Controllable deformation of silicon nanowires with strain up to 24%", Journal of Aplied Physics 107.12 (2010): 124314.

* cited by examiner

*Primary Examiner* — Arleen M Vazquez
*Assistant Examiner* — Lee Rodak
(74) *Attorney, Agent, or Firm* — Gates & Cooper LLP (57) ABSTRACT

A voltage sensing apparatus on a semiconductor substrate, including one or more inputs comprising metal contacts, an output comprising a laser transmitter, circuitry electrically connecting and interfacing the inputs to the output; and a power module. A method of fabricating the apparatus is also described.

20 Claims, 10 Drawing Sheets

Figure 1A-F. Overview of fabrication steps.

Figure 2A. Schematics of the device with a battery module for power supply.

Figure 2B Side View

Figure 3. Optical-fiber-intermediated design of the chip.

WIRELESS VOLTAGE SENSING DEVICE

CROSS REFERENCE TO RELATED APPLICATIONS

This application claims the benefit under 35 U.S.C. Section 119(e) of the following commonly-assigned application:

U.S. Provisional Patent Application Ser. No. 61/597,585, filed on Feb. 10, 2012, by Aditya Rajagopal, Chieh-Feng Chang, Akram Sarwat Sadek, Axel Scherer, and Raymond Jimenez, entitled "WIRELESS VOLTAGE SENSING DEVICE,", which application is incorporated by reference herein.

BACKGROUND OF THE INVENTION

1. Field of the Invention

This invention relates to (e.g., wireless) sensors and methods of fabrication of (e.g., wireless) sensors.

2. Description of the Related Art (Note: This application references a number of different publications as indicated throughout the specification by one or more reference numbers within brackets, e.g., [x]. A list of these different publications ordered according to these reference numbers can be found below in the section entitled "References." Each of these publications is incorporated by reference herein.)

Voltage sensors have widespread applicability. There is a need for miniaturized voltage sensors that are self sustained, robust, and have reduced power consumption. In biomedical applications, voltage sensors could be used to measure body functions or measure/characterize disease in tissue. For example, there is a need for bioimplantable voltage sensors.

Prior implantable recording devices are too large to be used in physiological experiments for behaving animals (e.g. Michigan-style neuroprobes, Utah-probes, etc.). This is because they are limited by the integration of components for data linking, powering, and sensing. By combining all three functions into a single geometry, the present invention can shrink the size of the implantables to a reasonable size scale.

SUMMARY OF THE INVENTION

One or more embodiments of the present invention disclose a voltage sensing apparatus, comprising a semiconductor substrate; one or more inputs, comprising metal contacts (e.g., platinum), on the substrate; an output, comprising a laser transmitter, on the substrate; circuitry, on the substrate, electrically connecting and interfacing (e.g., operably connecting) the inputs to the output; and a power module on the substrate and electrically connected, or operably connected, to the circuitry.

The metal contacts can be on one or more probe areas defined on the substrate.

The circuitry, the probe areas, the power module, and the laser transmitter can be within a surface area of the substrate of 4000 micrometers by 1000 micrometers or less and within a height of 200 micrometers or less.

The metal contacts can produce one or more voltage waveforms in response to one or more stimuli external to the substrate, the circuitry can convert the voltage waveforms into one or more signals, and the circuitry can modulates the laser transmitter's output with the signals. The laser transmitter's output can comprises electromagnetic radiation that transmits the signals off the semiconductor substrate and the apparatus.

The circuitry can comprise a voltage to current converter circuit that converts one or more voltage waveforms into one or more current waveforms, the voltage waveforms produced by the metal contacts in response to one or more stimuli external to the substrate.

The circuitry can comprise a modulator circuit that modulates the current waveforms to form one or more modulated waveforms.

The circuitry can comprise a mixer circuit that heterodynes the modulated waveforms to form one or more heterodyned waveforms.

A laser circuit can drive and modulates the laser transmitter with the heterodyned waveform, wherein the laser transmitter outputs electromagnetic radiation that transmits the heterodyned waveforms, representing the voltage waveforms, off the apparatus and the semiconductor substrate.

The modulator circuit can include a differential voltage controlled oscillator (VCO) and the current waveforms can modulate the VCO's center frequency to form one or more VCO waveforms. The mixer circuit can then heterodyne the VCO waveforms to form the heterodyned waveforms.

The modulator circuit can include a differential voltage controlled oscillator having instability (no direct current equilibrium).

The apparatus can further comprise a photodetector and a demodulator circuit connected to the photodetector, wherein the demodulator circuit demodulates the one or more signals and restores the voltage waveforms, when the photodetector is optically coupled to the laser transmitter.

The probe areas can have a length of 2000 micrometers or less, a width of 50 micrometers or less, and a triangular first end having a height of 5 micrometers or less.

The probe areas can be separated by 200 micrometers or less.

The metal contacts can be disposed in a diamond formation, comprise platinum, and have an area of 20 micrometers by 20 micrometers or less.

The circuitry can have a length and width of 500 micrometers or less.

The metal contacts can have an input impedance of more than 1 MegaOhm.

The power module can provide more than 1.4 milliwatts of input electrical power.

The circuitry can consume 400 microwatts of power or less and have voltage rails of +/−2V or less.

The laser transmitter can emit modulated electromagnetic radiation having a transmission frequency of 20 Megahertz or less.

The circuitry and laser can operate with a combined power of less than 400 microwatts, provided by the power module.

The power module can be a battery or photovoltaic device, for example.

The apparatus can include an optical fiber connected to the photovoltaic device; and a length of the optical fiber that extends to free space, or to a light source, when the substrate is implanted in an object, so that the photovoltaic device receives optical power along the optical fiber.

The apparatus can further comprise an optical fiber connected to the laser; and a length of the optical fiber that extends to free space when the substrate is implanted in an object, so that the laser transmitter transmits the electromagnetic radiation to free space along the optical fiber.

The apparatus can be biocompatible and bioimplantable on or inside a human tissue or a human being.

The laser can emit near infrared light, or light that is transmitted through a transmission window of human tissue.

One or more embodiments of the invention further disclose a method of fabricating a voltage sensing device, comprising providing one or more probe areas defined onto a semiconductor substrate; providing one or more metal contacts on the probe areas, wherein the metal contacts produce voltage waveforms in response to one or more stimuli external to the substrate; providing circuitry on the semiconductor substrate; providing a laser transmitter and laser circuit on the semiconductor substrate, electrically connected to the modulator circuit, wherein the laser transmitter transmits the modulated waveform off the substrate; and providing a power module on the semiconductor substrate and in electrical connection with the circuitry, wherein the power module provides power to the laser transmitter and the circuitry.

The method can further comprise lithographically defining and etching the one or more probe areas on the semiconductor substrate; depositing a thermal oxide on both sides of the substrate; depositing a stiction layer on the probe areas; defining and depositing the one or more metal contacts or pads on the stiction layer; depositing metallization to electrically connect the metal contacts to the circuitry; depositing metallization to electrically connect the circuitry to the laser transmitter; and depositing metallization to electrically connect the power module to the circuitry.

BRIEF DESCRIPTION OF THE DRAWINGS

Referring now to the drawings in which like reference numbers represent corresponding parts throughout:

FIGS. 1A-F illustrate an overview of the fabrication steps, according to one or more embodiments of the invention, wherein the in plane x and y directions and vertical z direction are indicated.

DETAILED DESCRIPTION OF THE INVENTION

In the following description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

Technical Description

I. Fabrication

Figure 1A:
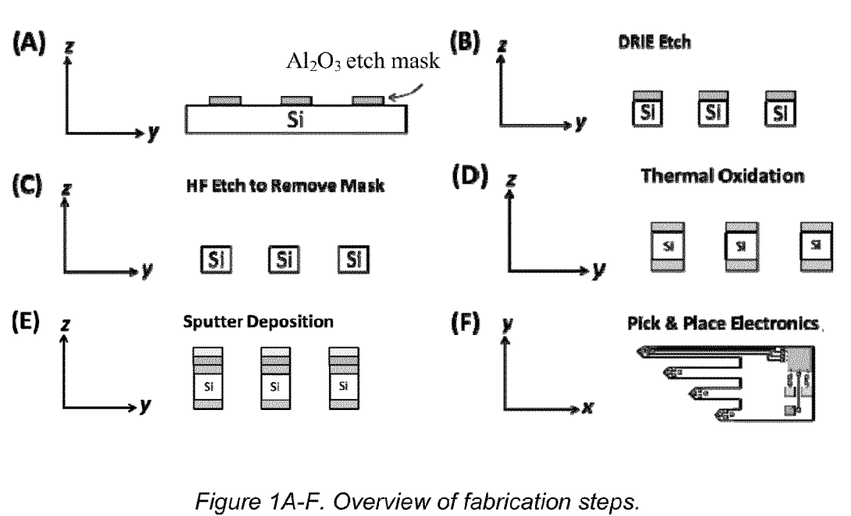

Step A: Probe Area Definition. Referring to FIG. 1A, aluminum oxide ($Al_2O_3$) is first deposited on the substrate (e.g., silicon Si) and patterned through lithography techniques to define the desired probe area.

Step B: Etching. The $Al_2O_3$ serves as an etch mask during deep reactive-ion etching (DRIE), in which unwanted portions of the wafer are removed, as illustrated in FIG. 1B. Details of these fabrication procedures can be found in the paper by Henry et al. [1].

Step C: Mask Removal. The $Al_2O_3$ etch mask is then removed in hydrofluoric acid (HF) as illustrated in FIG. 1C.

Step D: Thermal Oxidation. The substrate body of the probe is then sent into the oxidation furnace so that thermal oxide at a thickness of ~200 nanometers (nm) is grown on both sides, as illustrated in FIG. 1D.

Step E: Sputter deposition of materials/lithography/milling. On top of the chip, $Al_2O_3$ is again deposited as in FIG. 1E, this time as a stiction layer for better adhesion of the metal contacts.

Step F: Picking and placing Electronics/Wafer Bonding. Metal contact pads and connection wires are then deposited and defined on the $Al_2O_3$ layer.

The electronic circuit, the semiconductor laser, and the semiconductor photovoltaics (or the battery module) are then placed onto the substrate, and wire-bonding is performed for the electric interconnection, completing the fabrication steps as seen in FIG. 1F.

II. Device Embodiment and Physical Layout

Figure 2A:
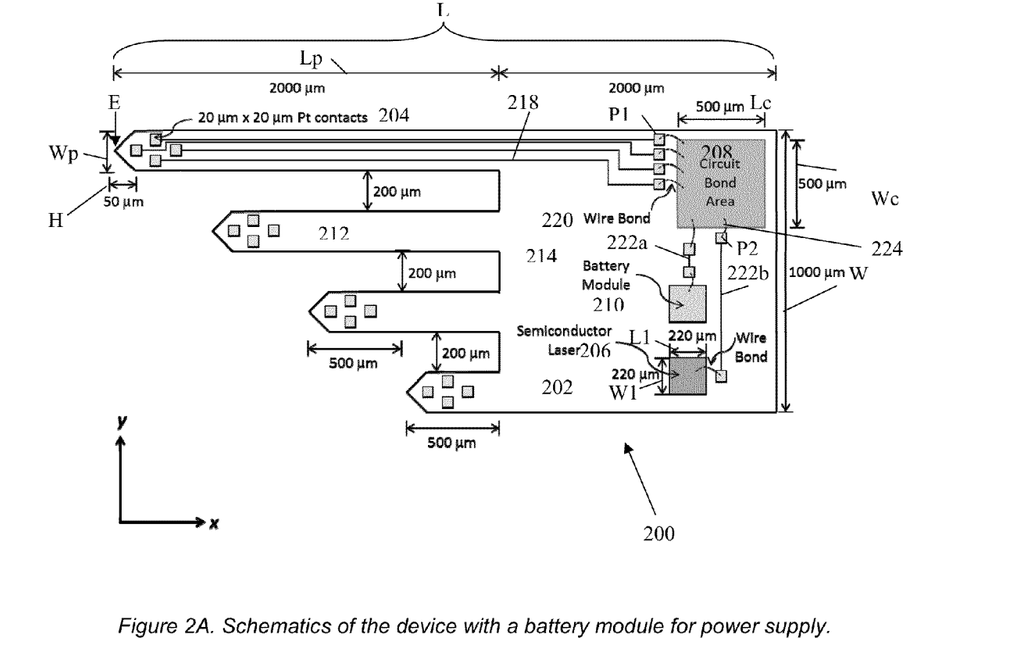
FIG. 2A illustrates a schematic top view of the device with a battery module for power supply, showing in-plane x and y directions, according to one or more embodiments of the invention.

FIG. 2 illustrates a voltage sensing apparatus/device 200 according to one or more embodiments of the invention. The apparatus 200 can be fabricated using one or more embodiments of the method of FIG. 1A-F, for example.

The device 200 comprises a substrate 202 (e.g., semiconductor substrate); one or more inputs comprising metal contacts 204; an output comprising a laser 206 transmitter (e.g., semiconductor laser); circuitry having a circuit bond area 208; and a power module 210.

The metal contacts 204, the laser transmitter 206, circuitry 208, and power module 210 are all on the substrate 202.

The circuitry 208 (e.g., one or more circuits or a group of circuits) electrically connects and interfaces the inputs to the output. The power module 210 (e.g. battery module) is electrically connected to the laser 206 transmitter and the circuitry 208 to provide power to the circuitry 208 and laser transmitter 206.

The metal contacts 204 are on one or more probe areas 212 (e.g., fingers) defined on the substrate 202.

The circuitry 208, the probe areas 212, the power module 210, and the laser 206 transmitter are within a surface area 214 of the substrate having a length L=4000 micrometers by a width W=1000 micrometers, and within a height 216 of 200 micrometers or less.

The probe areas 212 have a length Lp of 2000 micrometers, a width Wp of 50 micrometers, and a triangular first end E having a height H of 5 micrometers. The probe areas are disposed in an array, or rows of areas, and the length Lp of the next probe area is shorter than the previous one (by 500 micrometers). The probe areas 212 have a separation S of 200 micrometers.

The metal contacts 204 are disposed in a diamond formation, comprise platinum, and have an area of 20 micrometers by 20 micrometers.

One or more electrical connections electrically connect the metal contacts 204 to circuit 208, wherein the connections transmit one or more voltage waveforms sensed by the metal contacts 204 in response to one or more external stimuli. The connections include conductive lines, wires, pathways, striplines, or tracks 218, and wire bonds 220. The tracks 220 terminate at bond pads P1 and the wire bonds 220 connect the bond pads P1 to the circuitry 208.

One or more electrical connections electrically connect the power module 210 to the circuit 208 and the laser 206, wherein the connections transmit power from the power module 210 to the circuit 208 and the laser 206. The connections include tracks/wires 222a-b and wire bonds 224. The tracks 222a-b terminate at bond pads P2 and wire bonds 224 connect the bond pads P2 to the circuitry 208 and the laser 206. The connection 222b transmits modulated signals, produced in the circuit 208 in response to the voltage waveforms sensed by the metal contacts 204. The laser 206 outputs modulated electromagnetic radiation in response to the modulation signal transmitted along connection 222b.

The circuitry or circuit bond area 204 has a length Lc and width Wc of 500 micrometers, and the laser has a length L1 and width W1 of 220 micrometers.

Figure 2B:
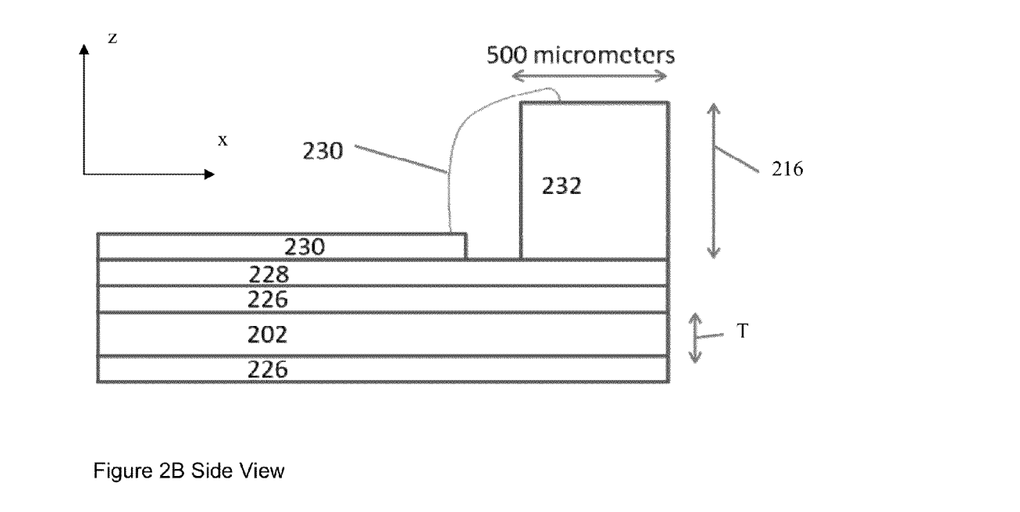
FIG. 2B is a sideview of a device, showing vertical z and in plane x directions, according to one or more embodiments of the invention.

FIG. 2B is a side-view of the chip, according to one or more embodiments of the invention. FIG. 2B illustrates the substrate 202, ~200 nanometer thick thermal oxide layer 226 deposited on both sides of the silicon (Si) substrate 202, a 200 nanometer thick aluminum oxide layer 228 deposited on the thermal oxide layer 226, and a 200 nanometer thick Pt layer 230 deposited and patterned on the aluminum oxide layer 228, to form the tracks 218 and pads P 1. The circuitry is on a bulk Si or GaAs chip 232 attached to the substrate 202. The thickness T of the silicon substrate 202 is ~25 micrometers.

In one or more embodiments, the metal contacts 204 have an input impedance of more than 1 MegaOhm. These input impedances can be achieved by using field-effect sensors that have oxide barrier layers (e.g. gate of a Metal Oxide Semiconductor Field Effect Transistor or MOSFET).

III. Powering of the Device

One or more embodiments of the invention propose three ways to power up the device: directly through the semiconductor photovoltaics on the chip, through an optical fiber onto the photovoltaics, and via a battery module connected to the chip.

In the first scenario, the photovoltaics are designed to respond to near-infrared (NIR) optical radiation for biological applications. The source of optical illumination is then tuned a wavelength that falls within a natural NIR optical window in biological tissues, such as ~800 nm. For non-biological applications there may be more liberty of choosing the wavelength of illumination by designing the photovoltaics correspondingly. Since coherence of the optical source is not critical to power up the device, the illumination can come from a laser, a light-emitting diode (LED), or even other traditional methods of lighting as long as it can generate enough electricity for the chip to operate. Wire-bonding is used to connect the photovoltaics to the electronic circuit and/or the semiconductor laser, depending on the system design.

Figure 3:
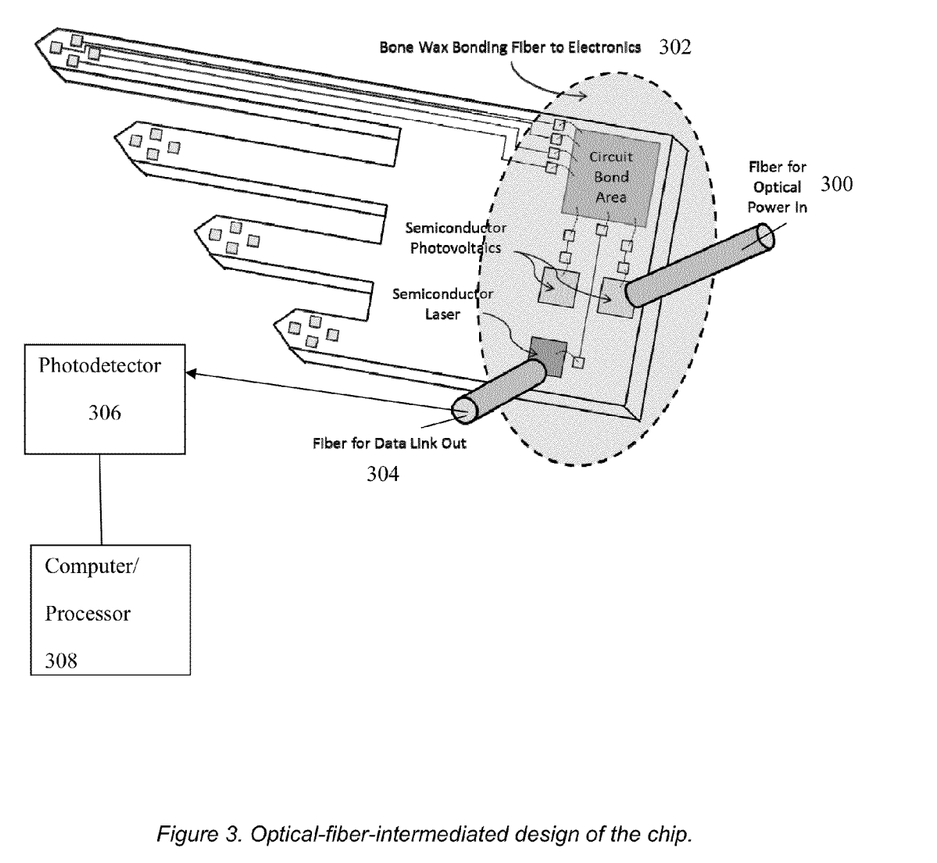
FIG. 3 is schematic top view of an optical fiber intermediated design of the chip, according to one or more embodiments of the invention.

A variation of this approach is to bring the optical illumination to the photovoltaics or PIN (e.g., PIN diode) through an optical fiber 300, which delivers the optical power from the free space outside of the object to be implanted (as illustrated in FIG. 3). The fiber 300 is bonded or mated to the chip 200 or photovoltaics (e.g., PIN) via bone wax 302 to ensure mechanical stability of the entire device 200. In this manner the illumination wavelength can be chosen based on the characteristics of the optical fiber 300, and the photovoltaics can be designed accordingly.

Another way is to connect a battery module to the chip to power up the device, as depicted in FIG. 2. The battery module stays with the object to be implanted so that the whole system is still wireless, and the module is designed for easy replacement for the battery.

IV. Optical Data Link

To optically transfer the measured signals back to the outside environment, one or more embodiments of the invention fabricate or bond semiconductor laser structures on to the substrate. The laser is wire-bonded to the electric circuit, which modulates the output of the laser as described previously. For biological applications, the laser is designed to operate at a wavelength that corresponds to one of the natural optical windows in biological tissues in the near-infrared and infrared (IR) regions. A few examples include, but are not limited to, the wavelengths of 850 nm, 920 nm, 1300 nm, 1550 nm, etc. Wavelength-division multiplexing (WDM) is utilized, so that output signals from different probes can be discerned from one another in the detection stage. In this way, a system of multi-channel sensors, by implanting chips designed to transmit back data at different optical wavelengths, is provided. WDM is achieved either from varying the laser design parameter(s), or from controlling the laser dynamics through the electronic circuit. Depending on the design, the laser can be either optically or electrically pumped.

One or more embodiments of the invention propose two ways for the semiconductor laser to send back the signals to the external photodetector.

One way is to directly transmit the laser beam through the tissues. Since the wavelength is chosen to be within a biological optical window, absorption and scattering can be reduced to decrease the overall signal attenuation. Depending on the desired configuration of external detectors, the semiconductor laser can be designed to spatially output the laser beam at a wide angle, or to emit at a narrow angle to increase the directionality of the data link.

The other way, as seen in FIG. 3, is to have a fiber 304 bonded or mated close to the laser 206 that relays the laser beam from the chip to the free space outside of the object to be implanted. In this way, the laser output is designed to be highly directional into the fiber end, and the laser spatial mode is designed to match the optical fiber mode. The wavelength can also be chosen for better propagation characteristics in the fiber.

The optical signal is eventually picked up by an external photodetector or even a sensor array. The detected signals are then sent to a computing device, where these data are demodulated by software and restored to the original voltage of measurement by the device.

FIG. 3 further illustrates a photodetector 306; and a demodulator circuit 308 or processor/computer connected to the photodetector 306, wherein the demodulator circuit/processor/computer 308 demodulates the one or more signals and restores the voltage waveforms, when the photodetector 306 is optically coupled to the laser transmitter 206 to receive the electromagnetic radiation transmitted or emitted by the laser 206.

In one or more embodiments, the laser transmitter 206 emits modulated electromagnetic radiation having a transmission frequency of 20 Megahertz or less.

V. Electronics

The metal contacts 204 can produce one or more voltage waveforms in response to one or more stimuli external to the chip, substrate 202, or apparatus/device 200. The circuitry 208 converts the voltage waveforms into one or more signals (e.g., electrical signals) and modulate the laser 206 transmitter's output with the signals. The laser transmitter's output then comprises electromagnetic radiation that transmits the signals off the chip, apparatus/device 200, or substrate.

Figure 4A:
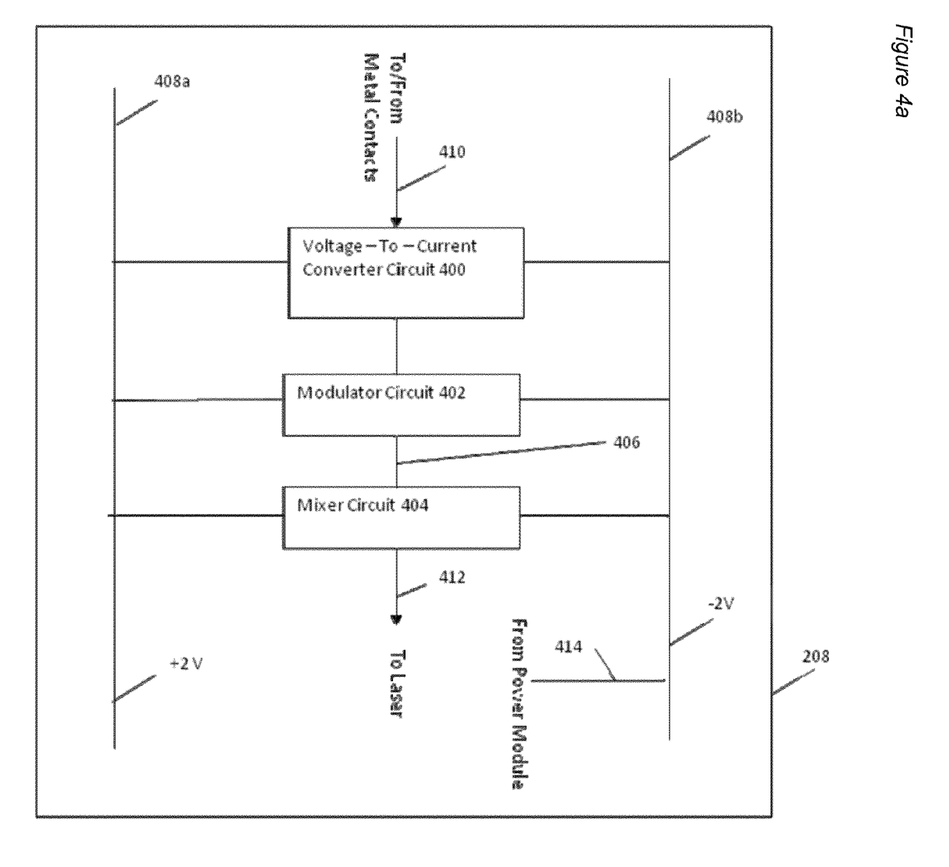
FIG. 4a illustrates circuitry, according to one or more embodiments of the invention.

FIG. 4a illustrates circuitry 208 according to one or more embodiments of the invention, including a voltage to current converter circuit 400, modulator circuit 402, mixer circuit 404, electrical connections 406 between the circuits, and voltage rails 408a-b. The circuits 400-404 and connections 406 are all operably connected.

The voltage to current converter circuit 400 converts one or more voltage waveforms into one or more current waveforms, the voltage waveforms produced by the metal contacts 204 in response to one or more stimuli external to the substrate 202. The modulator circuit 402 modulates the current waveforms to form one or more modulated waveforms. The mixer circuit 404 heterodynes the modulated waveforms to form one or more heterodyned waveforms.

The circuitry 208 can also further include a contact interface circuit comprising buffer, impedance matching/amplifier circuits for interfacing the circuit 208 with the metal contacts 204.

The circuitry 208 can further comprise a laser circuit that drives and modulates the laser transmitter 206 with the heterodyned waveform, and/or buffer/impedance matching/amplifier circuits for interfacing the circuit 208 with the laser. The laser circuit can drive and modulate the laser transmitter with the heterodyned waveform, wherein the laser transmitter outputs electromagnetic radiation that transmits the heterodyned waveforms, representing the voltage waveforms, off the apparatus and the semiconductor substrate.

Additional circuitry can be provided to impedance match or interface with the power module 210 or power circuit in the power module.

The circuitry 208 further comprises electrical connection 410 leading to wire bond 220 and the metal contacts 204, electrical connection 412 leading to wire bond 228 and the laser 206, and electrical connection 414 receiving power from the power module 210.

The circuits 402-410 are electrically connected 418 and the connections 418 can be via additional interfacing/buffering/amplifier circuits.

Figure 4B:
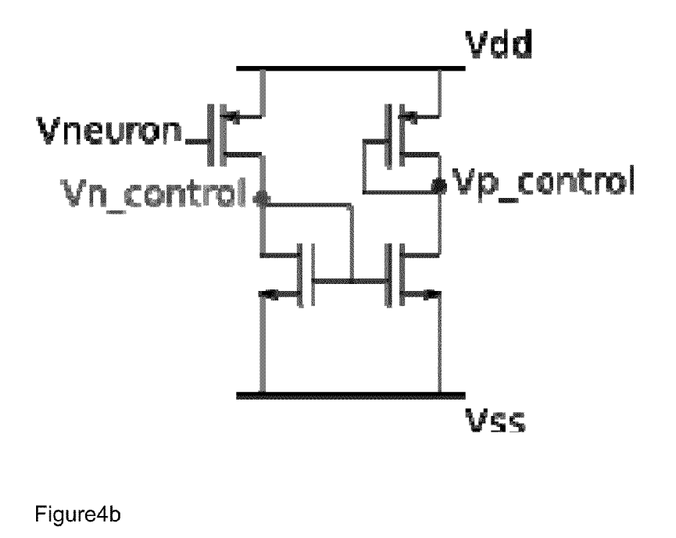
FIG. 4b illustrates neural interfacing done using current mirror that converts a neural voltage (Vneuron) into a current, according to one or more embodiments of the invention.

Neural interfacing can be done using current mirror that converts a neural voltage (Vneuron) into a current (see FIG. 4b). This current can be used to control a current starved delay elements in a local oscillator (see FIG. 4c). This effectively converts a neural voltage into a pulse waveform with a specific frequency. This frequency uniquely corresponds to the neural voltage (see FIG. 4d). This waveform is then transmitted through an optical datalink to an external reader for demodulation.

Vn_control and Vp_control are two control voltages that are generated by the neural voltage sense element (FIG. 4b). These voltages are used to control current starved delay elements in the Voltage Controlled Oscillator (VCO). As Vneuron changes, so do Vn_control and Vp_control. In1, In2, and Out1, Out2 are the inputs and outputs of the delay elements in these voltage controlled oscillators (VCOs), see FIG. 4e. Effectively, the magnitude of the neural signal affects the delay of an oscillation (and hence the frequency of the oscillation) through each of these delay element (FIG. 4e). These elements are configured in a "ring oscillator" geometry (FIG. 4c) to generate the required pulse waveform. FIG. 4d is the graph of simulated oscillation frequency as a function of simulated neural voltage. FIG. 4f is measured oscillation frequency as a function of input neural voltage.

Power Requirements and Circuit Performance

In one or more embodiments, the power module 210 provides 1.4 milliwatts or more of input electrical power, the circuitry 208 consumes 400 microwatts or less of power (e.g., Thermal Design Power for Complementary Metal Oxide Semiconductor or CMOS circuitry) and the circuitry has voltage rails 408a-b of +/−2V or less (408a is voltage rail at +2 Volts or less, and 408b is a voltage rail at −2 Volts or less). For example, the voltage rails can be +/−0.7 V.

Input optical power (e.g., via through-lens focusing) can be greater than 200 milliwatts.

The slew rate of the input can be optimized.

Differential Voltage Controlled Oscillator

In order to accommodate the tight power budget of a purely wireless system (wireless power and wireless data-linking), one or more embodiments include an optimally low power design for a differential voltage controlled oscillator (VCO). The oscillator design allows for guaranteed instability (i.e., no Direct Current (DC) equilibria), that is validated with both simulation and measurement (measurement and simulation data are shown in FIGS. 4f and 4d respectively). In one or more embodiments of the circuitry, voltage waveforms are converted into current waveforms, which in turn are used to modulate the VCO's center frequency. The VCO waveform (e.g., Frequency Modulated (FM) pulse) is then heterodyned for efficient transmission as well as frequency multiplexing. Each probe/circuit device can be electronically wired to transmit on a single channel allowing for single wavelength interrogation and multi channel, single wavelength reporting. One or more embodiments include a complete analog amplifier circuitry that operates under 10 microwatts (μW).

Accordingly, in one or more embodiments, the modulator circuit 402 of FIG. 4a can include a differential voltage controlled oscillator (VCO), wherein the current waveforms modulate the VCO's center frequency to form one or more VCO waveforms. The mixer circuit then heterodynes the VCO waveforms to form the heterodyned waveforms;

In one or more embodiments the circuitry 208 and laser 206 operate with a combined power of less than 400 microwatts, provided by the power module.

Figure 4C:
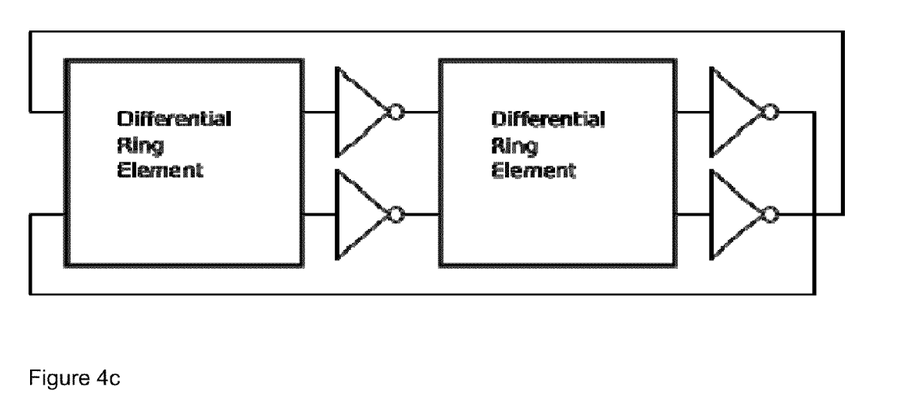
FIG. 4c illustrates a Voltage Controlled Oscillator (VCO) composed of differential, current starved delay elements, according to one or more embodiments of the invention.
Figure 4D:
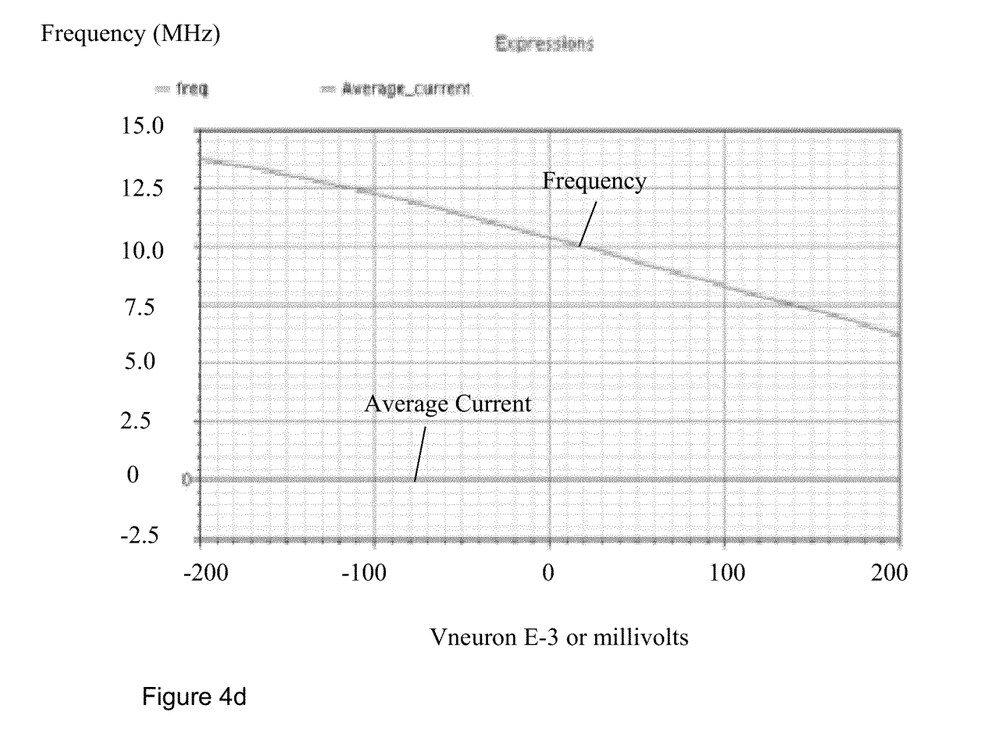
FIG. 4d is the graph of simulated oscillation frequency as a function of simulated neural voltage for the VCO according to one or more embodiments of the invention, wherein the y axis shows Frequency (Megahertz, MHz) and the x axis shows neural Voltage in millivolts.
Figure 4E:
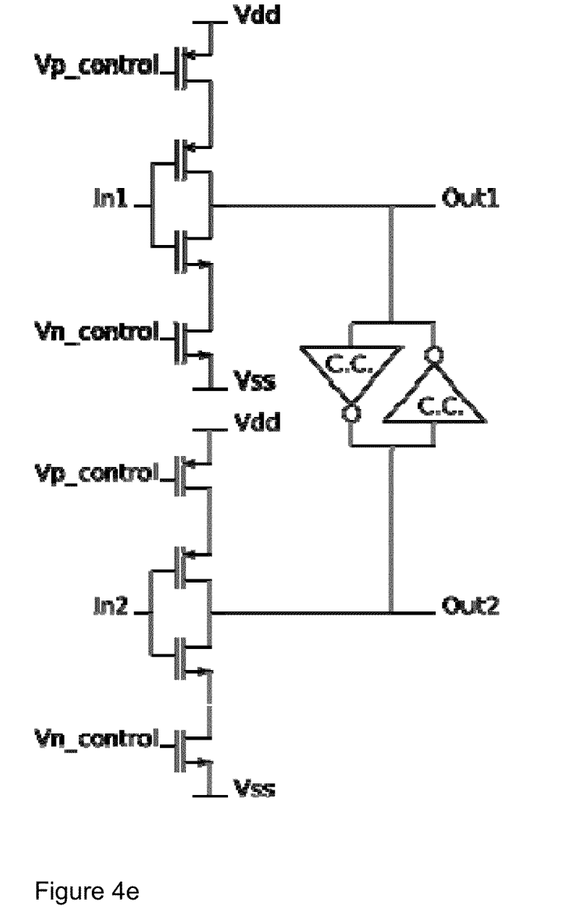
FIG. 4e illustrates a VCO composed of differential, current starved delay elements, according to one or more embodiments of the invention.
Figure 4F:
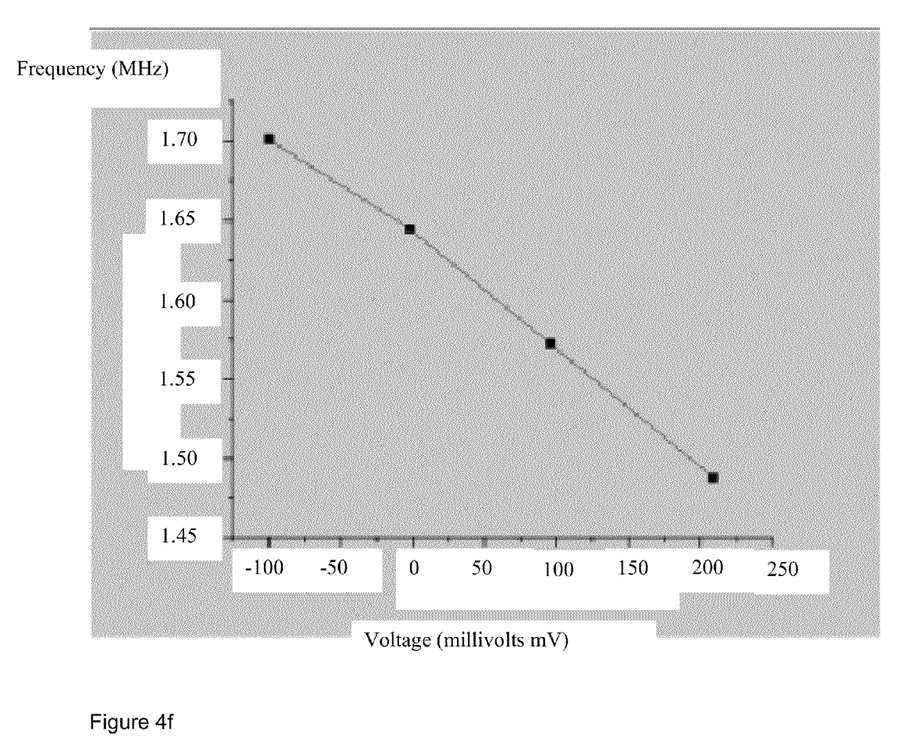
FIG. 4f is measured oscillation frequency as a function of input neural voltage, according to one or more embodiments of the invention, wherein the y axis shows Frequency (Megahertz, MHz) and the x axis shows neural Voltage in millivolts.

FIGS. 4c and 4e illustrate a VCO composed/comprised of differential, current starved delay elements (e.g., several delay elements or differential ring elements) daisy chained to make the VCO. The differential ring elements are a specific type of delay elements.

Low component count and size optimization results in minimal power consumption. The novelty in one or more embodiments of this design, is that it is designed to use the optimally minimal components. The designed voltage sensitivity is 1microvolt (μV). However, the present invention is not limited to this sensitivity.

VI. Process Steps for Fabrication

Figure 5:
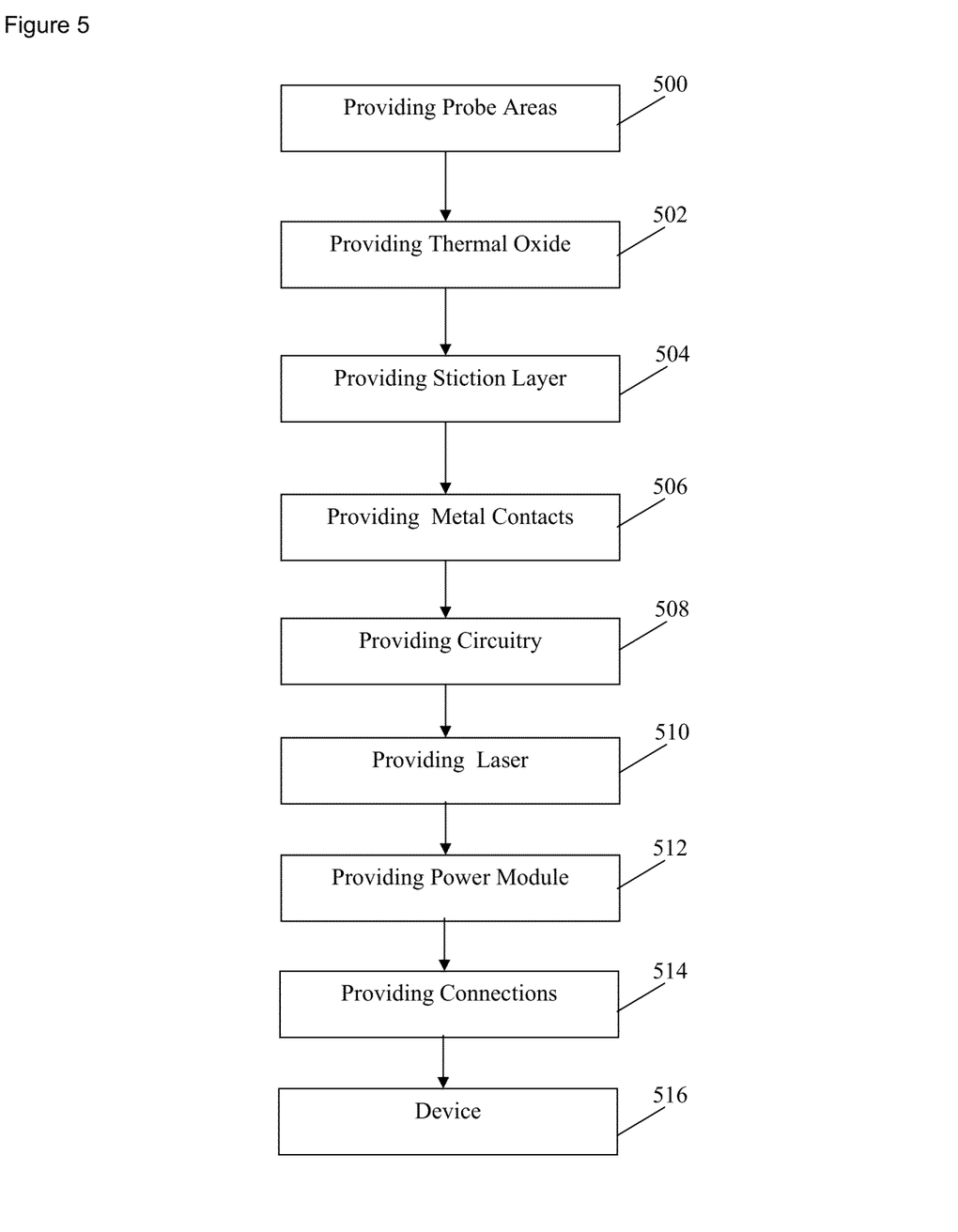
FIG. 5 illustrates a method of fabrication, according to one or more embodiments of the invention.

FIG. 5 is a flowchart illustrating a method of fabricating a voltage sensing apparatus, according to one or more embodiments of the invention.

Block 500 represents providing one or more probe areas defined onto a substrate. For example, the step can include lithographically defining and etching one or more probe areas on a semiconductor substrate (e.g., silicon).

Block 502 represents depositing a thermal oxide on both sides of the substrate.

Block 504 represents depositing a stiction layer on the probe areas.

Block 506 represents providing one or more metal contacts on the probe areas, wherein the metal contacts produce voltage waveforms/signals in response to one or more stimuli external to the substrate. For example, the step can include defining and depositing one or more metal contacts or pads on the stiction layer.

Block 508 providing circuitry on the substrate (e.g., picking and placing one or more circuits). The circuitry can include:

(i) a voltage to current converter circuit on the substrate, wherein the voltage to current converter circuit converts the voltage waveforms into current waveforms; and (ii) a modulator circuit on the substrate, wherein the modulator circuit modulates the current waveforms to form modulated waveforms/signals.

The circuitry can be bonded or otherwise attached on the substrate, or lithographically patterned and deposited using metallization on the substrate, for example.

Block 510 represents providing (e.g., picking and placing) a laser and laser circuit on the substrate, wherein the laser transmits the modulated waveform off the substrate or apparatus or device. The laser can be bonded or attached to the substrate, or otherwise deposited on the substrate, e.g., using lithographic patterning.

Block 512 represents providing (e.g., picking and placing) a power module comprising a power circuit on the substrate, that provides power to the laser and circuit/circuitry. The power module can be attached or fabricated/deposited on the substrate, e.g., using lithographic patterning.

Block 514 represents providing electrical connections/connection wires. For example, the step can include depositing metallization to electrically connect the metal contacts to the circuitry; depositing metallization to electrically connect the circuitry to the laser; and depositing metallization to electrically connect the power module to the laser and the circuitry.

Block 516 represents the end result, a voltage sensing device, as illustrated in FIG. 2 or 3. In one or more embodiments, the probe areas can have a length of 2000 micrometers or less, a width of 50 micrometers or less, a triangular first end having a height of 5 micrometers or less, and the probe areas are separated by 200 micrometers or less. In one or more embodiments, the metal contacts are disposed in a diamond formation, comprise platinum, and have an area of 20 micrometers by 20 micrometers or less. In one or more embodiments, the circuitry can have a length and width of 500 micrometers or less.

In one or more embodiments, the circuitry and laser operate with a combined power of less than 400 microwatts, provided by the power module.

Novel techniques in silicon etching enable the fabrication of this device. References to publications on novel techniques in alumina masking and etching include references [1-3].

Method of Sensing Voltages

Figure 6:
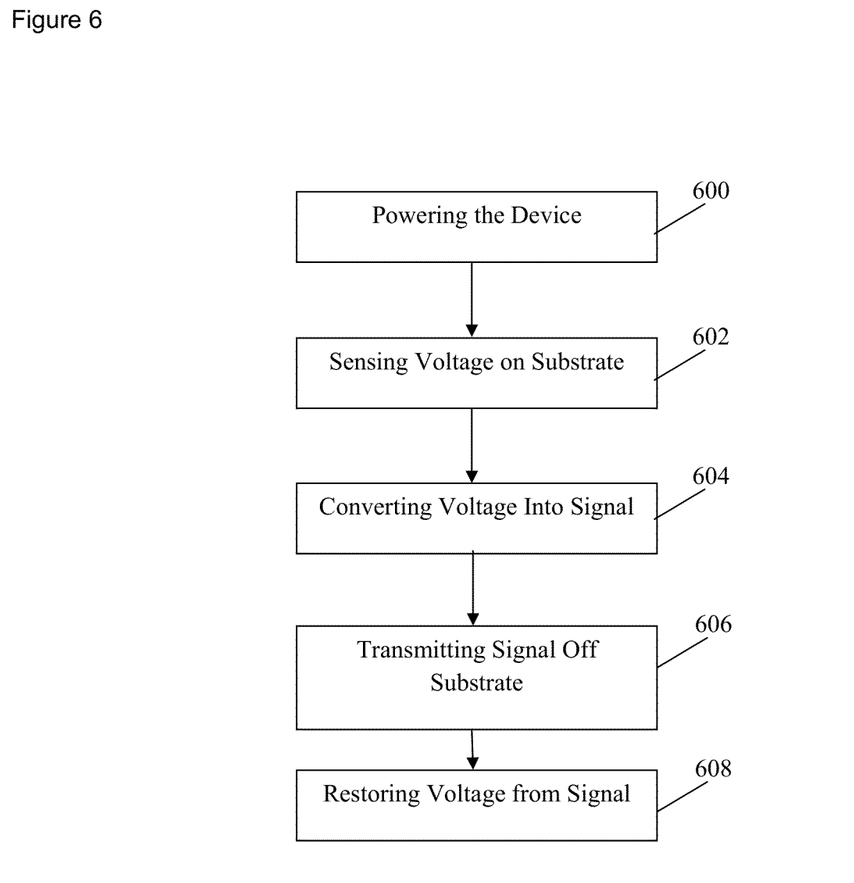
FIG. 6 illustrates a method of voltage sensing, according to one or more embodiments of the invention.

FIG. 6 illustrates a method of sensing voltages, according to one or more embodiments of the invention.

Block 600 represents powering a sensor on a substrate. The step can comprise providing a power module, comprising a power circuit, on the substrate and in electrical connection with circuitry. The power module can include a photovoltaic device on the substrate. An optical fiber can be optically connected to the photovoltaic device on the substrate, using a length of the optical fiber that extends to free space or to a light source (when the substrate is implanted in an object). In this way, the photovoltaic device receives optical power, or optical power in, along the optical fiber. The photovoltaic device or solar cell can have a p-type-intrinsic type-n-type (p-i-n) structure, for example.

Block 602 represents sensing voltages. The step may comprise providing metal contacts on probe areas on the substrate, wherein the metal contacts produce voltage waveforms in response to one or more stimuli external to the substrate or device.

Block 604 represents converting the voltage or voltage waveforms into one or more signals. The step may comprise providing circuitry on the substrate to convert the voltage to signals.

Block 606 represents transmitting the signal off the chip. The step may comprise providing a laser and laser circuit on the substrate, electrically connected to the circuitry, wherein the laser transmits the signal off the chip/device/substrate or apparatus. The circuitry can modulate the laser transmitter's output with the signals, and the laser transmitter's output comprises electromagnetic radiation that transmits the signals off the semiconductor substrate and the apparatus.

The step can include connecting an optical fiber to the laser, using a length of the optical fiber that extends to free space (when the substrate is implanted in an object). In this way, the laser transmitter transmits the electromagnetic radiation to free space along the optical fiber. The fiber can be mated to the laser or chip with bone wax for data link out.

Block 608 represents restoring the voltage from the signal. The step can comprise connecting a photodetector to a demodulator circuit. The demodulator circuit demodulates the one or more signals and restores the voltage waveforms, when the photodetector is optically coupled to the laser transmitter.

Possible Modifications

The apparatus 200 can be configured, selected, designed, or structured to be biocompatible and implantable on or inside a human being. The voltage signals detected can be neuron signals, for example.

The dimensions of the metal contacts 204, connections 218, circuitry 208, laser 206, and power module 210 can be changed. The apparatus 200 can be a nanoscale/microscale device, comprising nanoscale/microscale metal contacts 204, wires 218, circuitry 208, laser 206, and/or power module 210.

The circuitry 208 can be a processor (e.g., computer processor), integrated circuit, chip, Complementary Metal Oxide Semiconductor (CMOS), or application specific integrated circuit (ASIC), for example. The apparatus or device 200 can be an integrated circuit, chip, or integrated circuit chip.

A larger circuit area 208 can allow for time division multiplexing of the frequency modulated neural signal. Wavelength division multiplexing and frequency binning can still be done to increase data throughput.

REFERENCES

The following references are incorporated by reference herein.

[1] Henry, M.; Walavalkar, S.; Homyk, A.; Scherer, A. *Nanotechnology* 2009, 20, 4.

[2] Henry, M. D., et al. "Alumina etch masks for fabrication of high-aspect-ratio silicon micropillars and nanopillars." *Nanotechnology* 20.25 (2009): 255305.

[3] Walavalkar, Sameer S., et al. "Controllable deformation of silicon nanowires with strain up to 24%." *Journal of Applied Physics* 107.12 (2010): 124314-124314.

Conclusion

This concludes the description of the preferred embodiment of the present invention. The foregoing description of one or more embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. A voltage sensing apparatus, comprising:
   a semiconductor substrate having one or more probe areas each having a length of 2000 micrometers or less and a width of 50 micrometers or less;
   one or more inputs, comprising one or more metal contacts on the one or more probe areas, wherein the one or more metal contacts sense voltage comprising one or more voltage waveforms and in response to one or more stimuli;
   an output, comprising a laser on the substrate, wherein the laser can transmit one or more signals;
   circuitry, on the substrate, electrically connecting and interfacing the one or more inputs to the output, wherein the circuitry can convert the one or more voltage waveforms into the one or more signals;
   a power module on the substrate and electrically connected to the circuitry, wherein the power module can provide power to the circuitry and the laser; and
   wherein the circuitry, the probe areas, the power module, and the laser are within a surface area of the substrate of 4000 micrometers by 1000 micrometers or less.

2. The apparatus of claim 1, wherein:
   the circuitry, the probe areas, the power module, and the laser are within the surface area of the substrate of 3120000 micrometers squared or less and within a height of 200 micrometers or less.

3. The apparatus of claim 1, wherein the circuitry comprises:
   (i) a voltage to current converter circuit that converts the voltage into current;
   (ii) a modulator circuit including a differential voltage controlled oscillator (VCO), wherein the current modulates the differential VCO's center frequency to form one or more VCO waveforms;
   (iii) a mixer circuit that heterodynes the one or more VCO waveforms to form one or more heterodyned waveforms; and
   (iv) a laser circuit that drives and modulates the laser with the one or more heterodyned waveforms, wherein the laser outputs electromagnetic radiation that transmits the one or more signals comprising the one or more heterodyned waveforms off the apparatus and the semiconductor substrate; and
   wherein the circuitry consumes 400 microwatts of power or less; and the voltage sensing apparatus further comprises:
   a photodetector detecting the electromagnetic radiation and forming a detected signal in response thereto;
   a demodulator circuit connected to the photodetector, wherein the demodulator circuit demodulates the detected signal to reproduce the voltage.

4. The apparatus of claim 3, wherein the differential voltage controlled oscillator has instability (no direct current equilibrium).

5. The apparatus of claim 1, wherein:
   the substrate comprises silicon;
   the one or more probe areas are separated by 200 micrometers or less;
   the one or more metal contacts have an area of 20 micrometers by 20 micrometers or less; and
   the circuitry has a length of 500 micrometers or less and a width of 500 micrometers or less.

6. The apparatus of claim 1, wherein:
   the one or more metal contacts have an input impedance of more than 1 MegaOhm;
   the power module provides more than 1.4 milliwatts of input electrical power;
   the circuitry consumes 400 microwatts of power or less and has voltage rails of +/−2V or less; and
   the laser emits the one or more signals comprising modulated electromagnetic radiation having a transmission frequency of 20 Megahertz or less.

7. The apparatus of claim 1, wherein the circuitry and the laser operate with a combined power of less than 400 microwatts, provided by the power module.

8. The apparatus of claim 7, wherein the power module is a battery and the apparatus further comprises:
   an optical fiber connected to the laser so that the laser transmits the electromagnetic radiation along the optical fiber, or
   the laser emits near infrared light, or light that is transmitted through a transmission window of human tissue.

9. The apparatus of claim 1, wherein the power module is a photovoltaic device and the apparatus further comprises:
   a fiber connected to the photovoltaic device; and
   a length of the fiber that extends to a light source when the substrate is implanted, so that the photovoltaic device receives light along the fiber.

10. The apparatus of claim 1, wherein the apparatus is biocompatible and bioimplantable on or inside a human or animal tissue or a human or animal being and the voltage apparatus includes a microvolt voltage sensitivity.

11. The apparatus of claim 1, wherein the laser emits near infrared light, or light that is transmitted through a transmission window of human tissue.

12. The apparatus of claim 1, wherein the apparatus is an integrated semiconductor circuit chip biocompatible and bioimplantable on or inside tissue or a being such that the one or more metal contacts receive the one or more stimuli from neurons.

13. The apparatus of claim 1, wherein the semiconductor substrate comprises silicon and the silicon between adjacent probe areas is completely removed.

14. The apparatus of claim 1, wherein the semiconductor substrate comprises silicon and the probe areas comprise a height of at least 25 micrometers and/or the silicon and has a thickness of 25 micrometers or less.

15. The apparatus of claim 1, further comprising:
   a thermal oxide on both sides of the substrate;
   a stiction layer on the thermal oxide on the one or more probe areas;
   the one or more metal contacts defined on the stiction layer;
   first metallization electrically connecting the one or more metal contacts to the circuitry;
   second metallization electrically connecting the circuitry to the laser; and
   third metallization electrically connecting the power module to the circuitry.

16. The apparatus of claim 1, wherein the circuitry consumes 400 microwatts of power or less.

17. A method of fabricating a voltage sensing device, comprising:
   providing semiconductor substrate comprising silicon, having one or more probe areas each having a length of 2000 micrometers or less and a width of 50 micrometers or less;
   providing one or more inputs comprising one or more metal contacts on the probe areas, wherein the one or more metal contacts sense voltage comprising one or more voltage waveforms in response to one or more stimuli external to the substrate;
   providing circuitry on the semiconductor substrate, wherein the circuitry interfaces the inputs to an output and includes:
   (i) a voltage to current converter circuit on the substrate and electrically connected to the metal contacts, wherein the voltage to current converter circuit converts the one or more voltage waveforms into one or more current waveforms,
   (ii) a modulator circuit on the substrate and electrically connected to the voltage to current converter circuit, wherein the modulator circuit modulates the one or more current waveforms to form one or more modulated waveforms;
   providing the output comprising a laser on the semiconductor substrate, electrically connected to the modulator circuit, wherein the laser transmits the modulated waveform off the substrate; and
   providing a power module on the semiconductor substrate and in electrical connection with the circuitry, wherein the power module provides power to the laser and the circuitry.

18. The method of claim 17, further comprising:
   lithographically defining and etching the one or more probe areas on the semiconductor substrate;
   depositing a thermal oxide on both sides of the substrate;
   depositing a stiction layer on thermal oxide on the one or more probe areas;
   defining and depositing the one or more metal contacts on the stiction layer;
   depositing metallization to electrically connect the one or more metal contacts to the circuitry;
   depositing metallization to electrically connect the circuitry to the laser; and
   depositing metallization to electrically connect the power module to the circuitry.

19. A voltage sensing apparatus, comprising:
   a semiconductor substrate having a probe area having a length of 2000 micrometers or less and a width of 50 micrometers or less;
   a metal contact on the probe area, wherein the metal contact senses voltage, producing a voltage waveform in response to a stimulus;
   circuitry comprising:
      a current mirror that converts the voltage waveform into a current waveform; and
      current starved delay elements configured in a ring oscillator geometry in a voltage controlled oscillator (VCO), the current starved delay elements generating a pulse waveform in response to the current waveform and control voltages; and
      wherein the pulse waveform has a frequency corresponding to a magnitude of the voltage waveform; and
   a laser that transmits the pulse waveform to an external reader for demodulation so that the voltage waveform can be read; and
   a power module on the substrate and electrically connected to the circuitry, wherein the power module can provide power to the circuitry and the laser; and
   wherein the circuitry, the probe area, the power module, and the laser are within a surface area of the substrate of 4000 micrometers by 1000 micrometers or less.

20. The apparatus of claim 19, wherein:
   the ring oscillator geometry includes a first differential ring element and a second differential ring element each having first and second inputs and first and second outputs;
   the inputs and outputs of the differential ring elements are connected via inverters;
   the first and second outputs of the first differential ring element are connected to the first and second inputs of the second differential ring element, respectively, and
   the first output of second differential ring element is connected to the second input of the first differential ring element and the second output of second differential ring element is connected to the first input of the first differential ring element.

* * * * *